United States Patent [19]

Biller et al.

[11] Patent Number: 5,095,136
[45] Date of Patent: Mar. 10, 1992

[54] METHOD FOR PREPARING ISOPRENOID CYCLOPROPANE 1,1-DICARBOXYLATES AND DERIVATIVES THEREOF AND NOVEL INTERMEDIATES

[75] Inventors: Scott A. Biller, Ewing, N.J.; Cornelia Forster, Bensalem, Pa.

[73] Assignee: E. R. Squibb & Sons, Inc., Princeton, N.J.

[21] Appl. No.: 573,507

[22] Filed: Aug. 27, 1990

[51] Int. Cl.$^5$ .............................. C07C 69/74
[52] U.S. Cl. .................. 560/124; 562/506; 568/35; 568/700
[58] Field of Search .......... 560/124; 562/506; 568/35, 700

[56] References Cited

U.S. PATENT DOCUMENTS

| 3,445,499 | 5/1969 | Martel | 560/124 |
| 3,658,879 | 4/1972 | Julia | 560/124 |
| 3,997,586 | 12/1976 | Martel | 560/124 |
| 4,113,969 | 9/1978 | Lantzsch | 560/124 |
| 4,305,885 | 12/1981 | Hanack | 260/464 |
| 4,307,244 | 12/1981 | Ficini | 560/124 |
| 4,401,601 | 8/1983 | Martel | 560/124 |
| 4,642,372 | 2/1987 | Martel | 560/124 |

FOREIGN PATENT DOCUMENTS

| 49-66660 | 6/1974 | Japan | 560/124 |

OTHER PUBLICATIONS

Martel, J. et al., Bull. Soc. Chim. Fr. 1967, 985, DAS 1289046 (1969).
Arlt, D. et al., "Syntheses of Pyrethroid Acid", Angew. Chem. Int. Ed. Engl. 20, No. 9, 703-722 (Sep. 1981).
Campbell, R. V. M. et al., "Synthesis of (±)-Presqualene Alcohol, (±)-Prephytoene Alcohol, and Structurally Related Compounds", J. C. S. Perkin I, 1975, 897-913.
Hendrickson, J. B. et al., J. Am. Chem. Soc. 1974, 95, 2275-2276.
Capson, T. L. et al., "Synthesis of Ammonium Analogues of Carbocationic Intermediates in the Conversion of Presqualene Diphosphate to Squalene", J. Org. Chem. 1988, 53, 5903-5908.
Poulter, C. D. et al., "Squalene Synthetase. Inhibition by Ammonium Analogues of Carbocationic Intermediates in the Conversion of Presqualene Diphosphate to Squalene", J. Am. Chem. Soc. 1989, 111, 3734-3739.
Julia, M. et al., Guy-Rouault Bull. Soc. Chim. Fr. 1967, 1411.

Primary Examiner—Michael L. Shippen
Attorney, Agent, or Firm—Burton Rodney

[57] ABSTRACT

A process is provided for preparing isoprenoid cyclopropane 1,1-dicarboxylates and derivatives thereof including the corresponding monocarboxylate, monocarboxylic acid and alcohol derivatives thereof, all of which are useful in preparing squalene synthetase inhibitors which inhibit cholesterol biosynthesis, and also useful in preparing pyrethrin insecticides.

6 Claims, No Drawings

METHOD FOR PREPARING ISOPRENOID CYCLOPROPANE 1,1-DICARBOXYLATES AND DERIVATIVES THEREOF AND NOVEL INTERMEDIATES

FIELD OF THE INVENTION

The present invention relates to a method for preparing isoprenoid cyclopropane 1,1-dicarboxylates and derivatives thereof including the corresponding monocarboxylate, monocarboxylic acid and alcohol derivatives thereof, all of which are useful in preparing squalene synthetase inhibitors which inhibit cholesterol biosynthesis, and also useful in preparing pyrethrin insecticides and to novel intermediates prepared by such method.

BACKGROUND OF THE INVENTION

Martel, J. et al, Bull. Soc. Chim. Fr. 1967, 985, DAS 1289046 (1969), Arlt, D. et al, "Syntheses of Pyrethroid Acid," Angew. Chem. Int. Ed. Engl. 20, No. 9, 703–722 (Sept. 1981), at page 707 and Campbell, R.V.M. et al, "Synthesis of (±)-Presqualene Alcohol, (±)-Prephytoene Alcohol, and Structurally Related Compounds," J.C.S. Perkin I, 1975, 897–913, disclose the reaction of phenylsulfones with unsaturated monoesters to form transchrysanthemic acid esters according to the following reactions (Arlt et al).

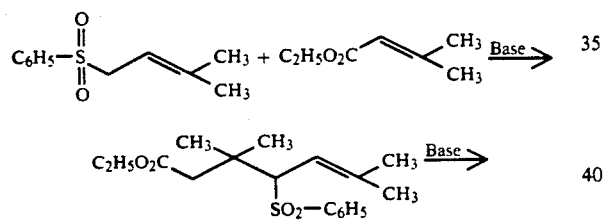

and to form presqualene and prephytoene systems (Campbell et al).

U.S. Pat. No. 4,305,885 describes the preparation of chrysanthemate derivatives via the addition of a perfluorobutyl sulfone to an unsaturated monoester according to the following reaction sequence:

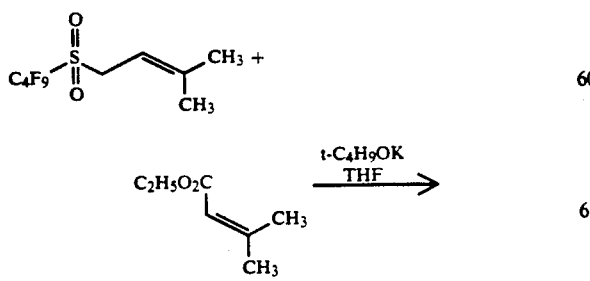

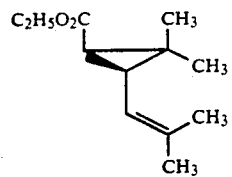

Julia, M. et al Guy-Rouault Bull. Soc. Chim. Fr. 1967, 1411 discloses the cyclopropanation of a 1,1-cyclopropane dicraboxylic ester and a phenyl sulfone according to the following reaction

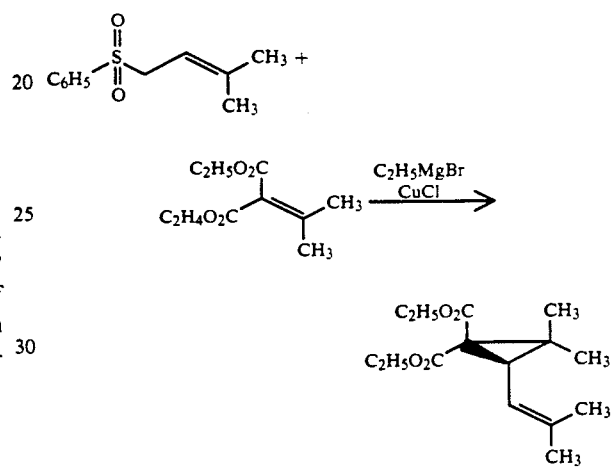

Hendrickson, J. B. et al, J. Am. Chem. Soc. 1974, 95, 2275–2276 disclose the conjugate addition of trifluoromethyl sulfones to provide cyclopropanes in a separate step as outlined below.

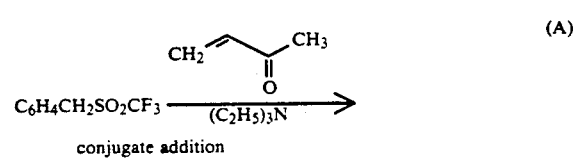

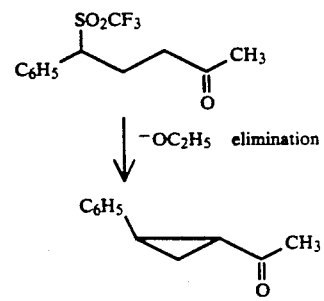

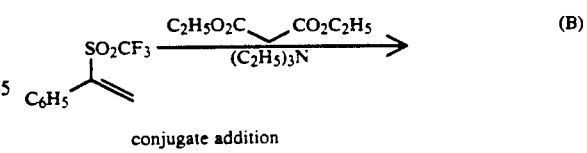

-continued

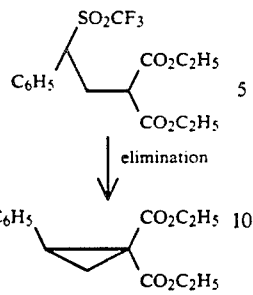

Capson, T. L., et al, "Synthesis of Ammonium Analogues of Carbocationic Intermediates in the Conversion of Presqualene Diphosphate to Squalene," J. Org. Chem. 1988 53, 5903-5908 disclose the preparation of certain squalene synthetase inhibitors of the structure

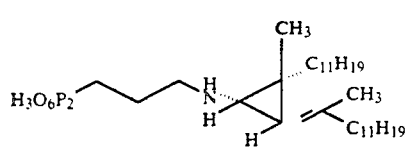

which are prepared from an isoprenoid cyclopropane monocarboxylate of the structure

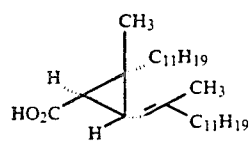

Poulter, C. D. et al, "Squalene Synthetase. Inhibition by Ammonium Analogues of Carbocationic Intermediate in the Conversion of Presqualene Diphosphate to Squalene," J. Am. Chem. Soc. 1989, 111, 3734-3739, disclose the testing of such squalene synthetase inhibitors.

DESCRIPTION OF THE INVENTION

In accordance with the present invention, a method is provided for preparing isoprenoid cyclopropane, 1,1-dicarboxylates and derivatives thereof which method is simple, clean and efficient and produces product in substantially pure form.

The method of the invention for preparing isoprenoid cyclopropane 1,1-dicarboxylates of the structure

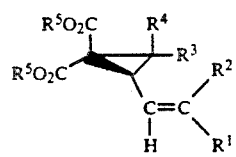

wherein $R^1$, $R^2$, $R^3$ and $R^4$ are the same or different and are independently selected from $CH_3$ or

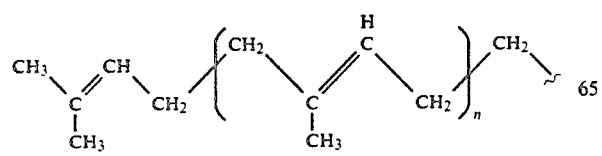

n is 0 to 3, and $R^5$ is lower alkyl, includes the step of treating an allylic fluorinated sulfone of the structure II

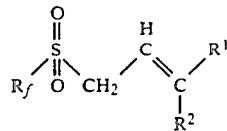

wherein $R_f$ is $CF_3(CF_2)_m$ where m is 0 to 5, and $R^1$ and $R^2$ are as defined above, with an alkene 1,1-dicarboxylate of the structure

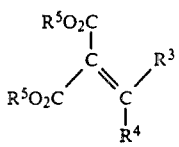

wherein $R^3$, $R^4$ and $R^5$ are as defined above, in the presence of a base, at a reduced temperature of within the range of from about $-80°$ to about $25°$ C., to form the isoprenoid cyclopropane 1,1-dicarboxylate.

In addition, in accordance with the present invention, a method is provided for forming an isoprenoid cyclopropane monocarboxylate of the structure

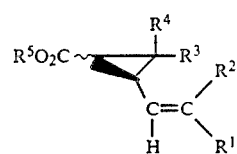

wherein $R^1$, $R^2$, $R^3$, $R^4$ and $R^5$ as defined above, by treating an isoprenoid cyclopropane 1,1-dicarboxylate I with a tetraalkylammonium acetate V

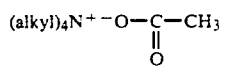

under an inert atmosphere, to form monocarboxylate IV.

The monocarboxylate IV may then be hydrolyzed to the corresponding monocarboxylic acid VI

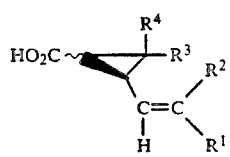

The monocarboxylate IV may also be reduced to the corresponding alcohol VII

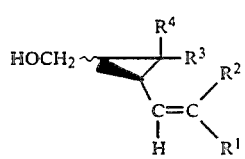

Further in accordance with the present invention, the starting allylic fluorinated sulfone II may be prepared by treating an allylic halide of the structure VIII

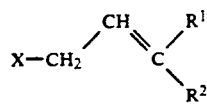

wherein $R^1$ and $R^2$ are as defined above, and X is Br, Cl or I (preferably Br) with a triflinate of the structure IX

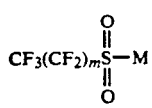

wherein M is an alkali metal such a K, Na or Li, (K preferred) optionally in the presence of 18-crown-6 or 15-crown-5, and an inert organic solvent such as dimethylformamide (DMF), dimethylsulfoxide (DMSO), hexamethylphosphoramide (HMPA), tetrahydrofuran (THF) or mixtures thereof.

The allylic fluorinated sulfone of the structure IIA

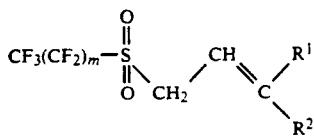

wherein at least one of $R^1$ and $R^2$ is

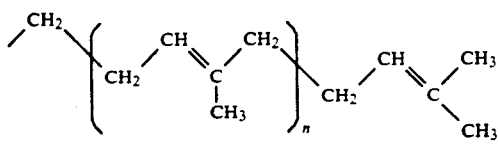

is a novel compound.

In the method of the invention for preparing isoprenoid cyclopropane 1,1-dicarboxylate I, the base-promoted condensation of the allylic fluorinated sulfone II with the alkene 1,1-dicarboxylate III is carried out in the presence of an inert organic solvent such as tetrahydrofuran, diethyl ether, preferably tetrahydrofuran, and a strong base such as n-butyllithium or lithium diisopropylamide, preferably n-butyllithium, and an anion activator, namely, HMPA or N,N'-dimethylpropyleneurea (DMPU), preferably HMPA (which activates the anion of sulfone II towards conjugate addition). The above reaction is carried out at reduced temperature of within the range of from about $-80°$ C. to about 25° C., and preferably from about $-78°$ C. to about 0° C., under an inert atmosphere such as argon or nitrogen, preferably argon.

The allylic fluorinated sulfone II will be employed in a molar ratio to the alkene 1,1-dicarboxylate III within the range of from about 0.7:1 to about 1.3:1.

The base will be employed in a molar ratio to sulfone II of within the range of from about 0.9:1 to about 1.1:1, while the sulfone anion activator will be employed in a molar ratio to sulfone II of within the range of from about 1:1 to about 5:1, and preferably about 2:1.

Where $R^3$ and $R^4$ in the alkene 1,1-dicarboxylate II differ, an isomeric mixture of product will be obtained which may be separated by conventional procedures such as crystallization or chromatography to give the desired isomer.

The above method produces an unexpectedly high yield of substantially clean product in a single step with minimal side products.

The diester I can be decarboxyalkylated to provide monocarboxylate IV wherein diester I is treated with tetraalkylammonium acetate V, preferably tetramethylammonium acetate, in the presence of an inert solvent such as dimethylsulfoxide (DMSO), xylene or dimethylformamide, preferably DMSO, at a temperature of within the range of from about 80° to about 180° C., and preferably from about 130° to about 150° C., under an inert atmosphere such as argon or nitrogen, preferably argon. Where $R^3$ and $R^4$ differ, the resulting product will include a mixture of isomers which may be separated by conventional means as described hereinbefore.

The monoester V can be hydrolyzed to acid VI by treating V with a base such as sodium hydroxide, potassium hydroxide, or lithium hydroxide, preferably sodium hydroxide, in the presence of an inert organic solvent such as tetrahydrofuran, dioxane, ethanol or methanol, to form the alkali metal salt, followed by neutralizing with an acid, such as dilute hydrochloric acid or oxalic acid, to form the corresponding acid VI.

The monoester V can be reduced to the corresponding alcohol VII by treating V with a reducing agent such as lithium aluminum hydride, lithium borohydride, or diisobutylaluminum hydride in the presence of an inert organic solvent such as diethyl ether, tetrahydrofuran or toluene, at a reduced temperature of from about $-20°$ C. to about 25° C.

The starting allylic fluorinated sulfone II may be prepared by reacting allylic halide VIII with triflinate IX in the presence of 18-crown-6 or 15-crown-5 and an inert organic solvent such as dimethylformamide, DMSO, HMPA, THF or mixtures thereof, employing a molar ratio of VIII:IX of within t:e range of from about 0.7:1 to about 1.2:1.

The allylic halide may be prepared as described in U.S. Patent No. 4,871,721, for example, as described in Example 1, Part A.

Examples of starting allylic halide VIII which may br employed herein include, but are not limited to, the following:

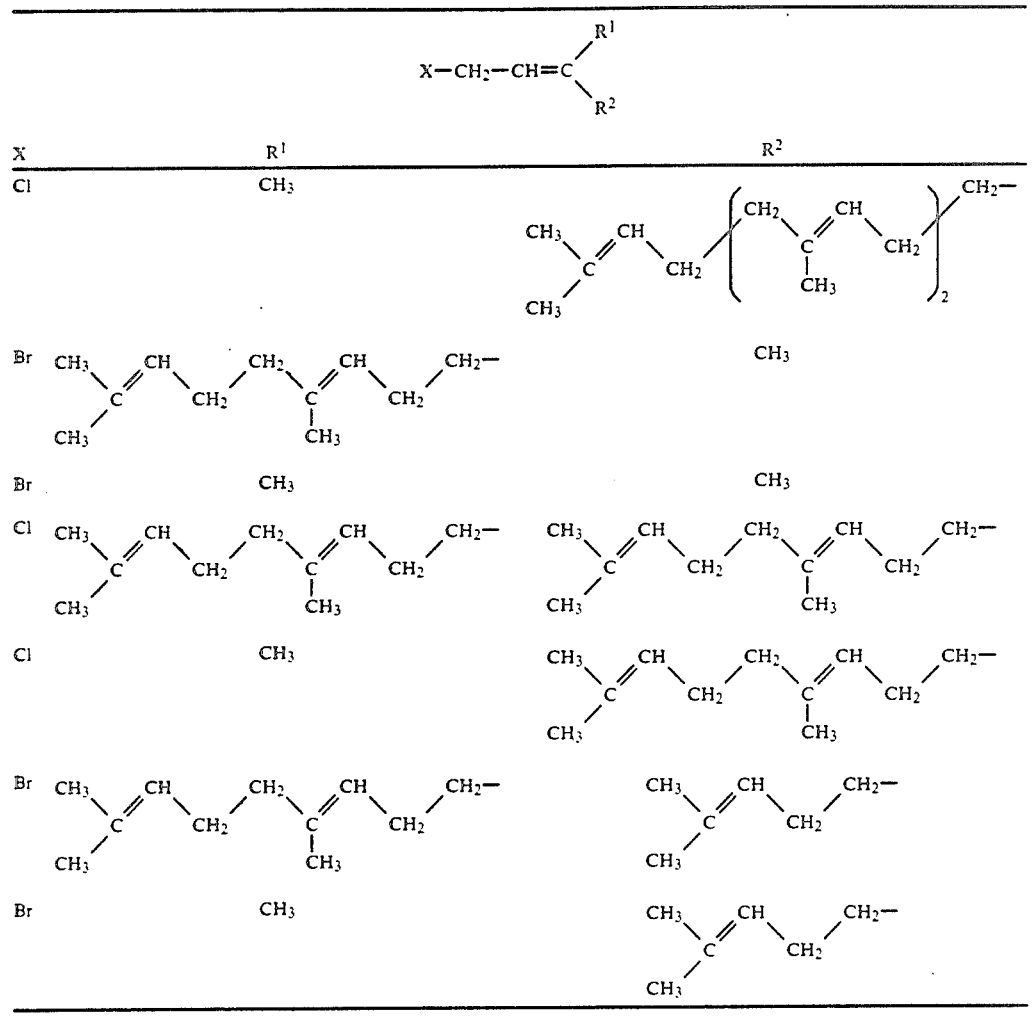

Examples of starting triflones IX which may be employed herein include, but are not limited to, the following:

$$CH_3(CF_2)_m-\overset{O}{\underset{O}{\overset{\|}{\underset{\|}{S}}}}-M$$

| m | M |
|---|---|
| 0 | K |
| 1 | Na |
| 2 | K |

-continued $$CH_3(CF_2)_m-\overset{O}{\underset{O}{\overset{\|}{\underset{\|}{S}}}}-M$$

| m | M |
|---|---|
| 3 | K |
| 4 | Li |
| 5 | K |

Examples of starting alkene 1,1-dicarboxylate III which may be employed herein include, but are not limited to, the following:

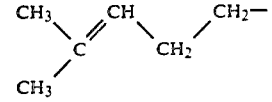

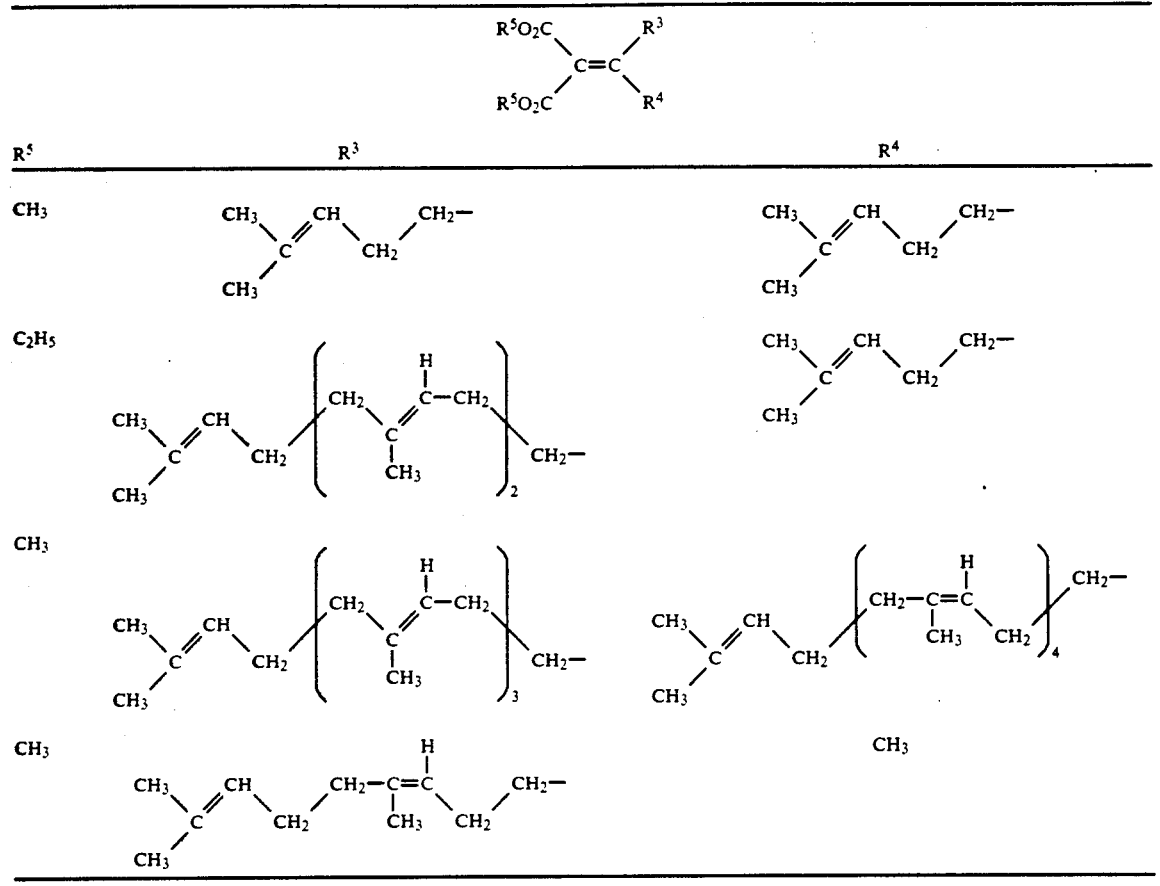

The following working examples represent preferred embodiments of the present invention. Unless otherwise indicated, all temperatures are expressed in degrees centigrade.

EXAMPLE 1

(E,E,E)-2-(4,8-Dimethyl-3,7-nonadienyl)-2-methyl-3(2,6,10-trimethyl-1,5,9-undecatrienyl)-1,1-cyclo-propanedicarboxylic acid, dimethyl ester A. (E)-(1,5,9-Trimethyl-4,8-decadienylidene)-propanedioic acid, dimethyl ester To 200 mL of tetrahydrofuran at 0° C. under argon was added over 45 minutes a solution of 102 mL (102 mmol, 2 equiv) of 1 M titanium (IV) chloride in $CH_2Cl_2$, resulting in the formation of a granular, yellow precipitate. The reaction mixture was treated with 11.5 mL (51 mmol) of geranyl acetone and 5.8 mL (51 mmol) of dimethyl malonate, followed by the addition over one hour of a solution of 16.5 mL (204 mmol, 4 equiv) of pyridine in 35 mL of tetrahydrofuran. The resulting brown, sludgy mixture was stirred 16 hours at room temperature, then quenched with 25 mL of water and diluted with 600 mL of diethyl ether. The organic phase was washed with 100 mL of saturated $NaHCO_3$, 100 mL of $H_2O$ and 100 mL of brine, dried over $MgSO_4$ and evaporated to give 15.6 g of crude material as an orange oil. Purification by flash chromatography on 1.5 kg of silica gel, eluted with 2:98 ethyl acetate: hexane provided 9.34 g (60%) of title diester as a yellow oil. TLC Silica gel (5:95 ethyl acetate: hexane) $R_f=0.24$.

IR ($CCl_4$) 2968, 2951, 2926, 2919, 2857, 1723, 1635, 1434, 1376, 1284, 1244, 1221, 1151, 1063 cm$^{-1}$ $^1$H-NMR ($CDCl_3$, 270 MHz): δ 5.13 (t, 1H, J=7.0 Hz), 5.09 (t, 1H, J=7.0 Hz), 3.76 (s, 6H), 2.38 (t, 2H, J=7.0 Hz), 2.20 (q, 2H, J=7.0 Hz), 2.08 (s, 3H), 1.9–2.1 (m, 4H), 1.68 (s, 3H), 1.61 (s, 3H), 1.60 (s, 3H), ppm.

Mass Spec (CI—$CH_4/N_2O$,=ions) m/e 337 (M+$C_2H_5$), 309 (M+H), 307 (M+H—$H_2$)

Anal. Calc'd for $C_{18}H_{28}O_4$: C, 70.10; H, 9.15. Found: C., 70.16; H, 9.43.

B. (E,E)-3,7,11-Trimethyl-2,6,10-dodecatrienyl bromide (Farnesyl bromide)

A solution of 1.00 g (4.5 mmol) of E,E-farnesol (Aldrich, further purified by flash chromatography) in 10 mL of distilled ether at 0° C. under argon in the dark was treated dropwise with a solution of 195 μL (2.05 mmol, 0.45 eq.) of $PBr_3$ in 2 mL of ether. The resultant mixture was stirred at 0° C. for one hour, then quenched with water and separated. The organic phase was washed with 5 mL of $H_2O$, 5 mL of saturated $NaHCO_3$, and 5 mL of brine, dried over $Na_2SO_4$ and evaporated to give 1.26 g (98%) of crude bromide as a clear oil. TLC Silica (2:8 ethyl acetate:Hexane) $R_f=0.69$ (decomposes).

$^1$H NMR (CDC13): δ 5.52 (t, 1H, J=8.5 Hz), 5.08 (m, 2H), 4.01 (d, 2H), 1.9–2.2 (m, 8H), 1.73 (s, 3H), 1.68 (s, 3H), 1.60 (s, 6H) ppm.

C. (E,E)-(3,7,11-Trimethyl-2,6,10-dodecatrienyl)(trifluoromethyl)sulfone

A mixture of 12.20 g (42.8 mmol) of Part B farnesyl bromide, 8.0 g (52 mmol, 1.2 equiv) of potassium trifluoromethylsulfinate (Parrish Chemical) and 1.00 g (4.3 mmol, 0.1 equiv) of 18-crown-6 in 200 mL of dry dimethylformamide was stirred for 66 hours. The dimethylformamide was evaporated at reduced pressure with minimal warming. The residue was dissolved in 600 mL of diethyl ether and washed with three 70 mL portions of H20 and 70 mL of brine, dried over MgSO₄ and evaporated. Purification by flash chromatography on 200 g of Merck 9385 silica eluted with 15:85 CH₂Cl₂: hexane provided 1.35 g of mixed fractions and 9.02 g (63%) of pure product. The mixed fractions were rechromatographed on 60 g of silica gel, eluting with 15:85 CH₂Cl₂: hexane to provide 0.95 g (7%) of pure title product. The two portions of pure title triflone product were combined: 9.97 g (70%) of a pale yellow oil.

TLC Silica gel (15:85 CH₂Cl₂ hexane) $R_f$=0.10.

IR (CCl₄) 2968, 2924, 2917, 2855, 1660, 1447, 1372, 1223, 1211, 1197, 1123, 623 cm$^{-1}$.

$^1$H-NMR (CDCl₃, 270 MHz): 5.25 (t, 1H, J=7.62 Hz), 5.08 (m, 2H), 3.93 (d, 2H, J=7.62 Hz), 1.9-2.2 (m, 8H), 1.78 (s, 3H), 1.68 (s, 3H), 1.60 (s, 6H) ppm.

Mass Spec (CI-NH₃,+ions) m/e 356 (M+NH₄), 338 (M), 69.

Anal. Calc'd for C₁₆H₂₅F₃O₂S: C, 56.78; H, 7.45; F, 16.84 Found: C, 56.86; H, 7.54; F, 16.41.

D.
(E,E,E)-2-(4,8-Dimethyl-3,7-nonadienyl)-2-methyl-3-(2,6,10-trimethyl-1,5,9-undecatrienyl)-1,1-cyclopropanedicarboxylic acid, dimethyl ester A solution of 9.930 g (29.3 mmol) of Part C triflone and 10.2 mL (59.6 mmol, 2 equiv) of hexamethylphosphoramide (distilled) in 150 mL of tetrahydrofuran at −78° C. under argon was treated over 0.5 hours with a solution of 20.5 mL (32.5 mmol, 1.1 equiv) of 1.6 M n-butyllithium in hexanes. After 0.5 hours at −78° C., a solution of 9.96 g (32.5 mmol, 1.1 equiv) of Part A diester in 45 mL of tetrahydrofuran was added over 0.5 hours. The reaction mixture was stirred for one hour at −78° C. and five hours at 0° C., then quenched with NH₄Cl and diluted with 700 mL of diethyl ether. The organic phase was washed with five 50 mL portions of H₂O, and 50 mL of brine, dried over MgSO₄ and evaporated to yield 18.36 g of crude product. Purification by flash chromatography on 1 kg of silica gel, eluted with 3:97 diethyl ether:hexane provided 12.67 g (84%) of pure title diester as a clear, colorless oil. The title diester was isolated as an inseparable mixture of isomers of approximately 1.6:1 (1):(2). These assignments were made on the basis of NOE studies on the mixture.

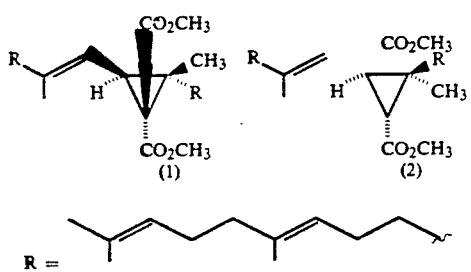

TLC Silica gel (1:1 toluene:hexane) $R_f$0.17.

IR (CCl₄) 2966, 2949, 2925, 2916, 2855, 1731, 1448, 1434, 1382, 1377, 1296, 1239, 1196, 1164, 1103, 1069 cm$^{-1}$.

$^1$H-NMR 400 MHz): δ 5.40 (dd, J=8, 1.1 Hz), 5.35 (d, J=8 Hz), 5.21 (m, 4H), 3.41 (s), 3.40 (s), 3.38 (s), 3.37 (s), 2.81 (d, J=8 Hz), 2.75 (d, J=8 Hz), 2.0-2.2 (m, 14H), 1.72 (s), 1.71 (s), 1.67 (s, 6H), 1.58, 1.56, 1.55 (three s, 12H), 1.44 (s), 1.26 (s) ppm.

Mass Spec (Cl-CH₄,+ions) m/e 541 (M+C₂H₅), 513 (M+H), 481.

Anal. Calc'd for C₃₃H₅₂O₄: C, 77.30; H, 10.22 Found: C, 77.08; H, 10.43.

EXAMPLE 2

A. [1α,2β(E),3α(E,E)]-2-Methyl-3-(2,6,10-trimethyl-1,5,9-undecatrienyl) cyclopropanecarboxylic acid, methyl ester B. [1α,2α(E),3α(E,E)]-2-Methyl-3-(2,6,10-trimethyl-1,5,9-undecatrienyl) cyclopropanecarboxylic acid, methyl ester C. [1α,2β(E),3β(E,E)]-2-Methyl-3-(2,6,10-trimethyl-1,5,9-undecatrienyl) cyclopropanecarboxylic acid, methyl ester D. [1α,2α(E),3β(E,E)]-2-Methyl-3-(2,6,10-trimethyl-1,5,9-undecatrienyl) cyclopropanecarboxylic acid, methyl ester A solution of 12.61 g (24.6 mmol) of Example 1 diester and 43.6 g (32.7 mmol, 13 equiv) of tetramethylammonium acetate in 150 mL of dimethylsulfoxide was stirred at 140-145° C. under argon for 18 hours. After cooling, the dark solution was diluted with 700 mL of diethyl ether and washed with five 100 mL portions of H₂O and 100 mL of brine, drived over MgSO₄ and evaporated to give 11.017 g of a brown-orange oil containing four isomers: 2A (F$_f$0.56), 2B (R$_f$0.44) 2C (R$_f$ 0.36), and 2D (R$_f$ 0.27), TLC Silica gel (1:1 toluene: hexane).

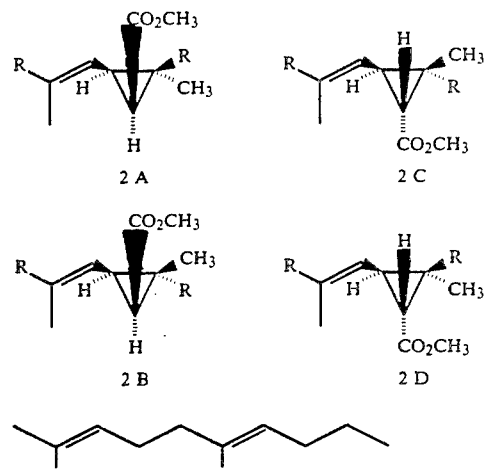

$^1$H-NMR of the crude mixture shows an approximate isomer ratio of A:B:C:D=15:30:35:20. Purification by flash chromatography on 1.2 kg of Merck 9385 silica, eluted with 2:8 toluene:hexane provided a total yield of 9.513 g (85%) of title decarboxylated product. Following amounts of isomers were isolated independently: 2A: 998 mg (9%), 2B+2C: 5,685 g (51%), and 2D: 1.940 g (17%). A fraction containing both 2C and 2D was rechromatographed on 50 g Merck 85 silica, eluting with 2:8 toluene:hexane to provide an additional 83 mg (0.7%) of isomer 2D. By $^1$H-NMR analysis, isomer 2D contained less than 5% of isomer 2C.

Data for 2D

IR (CCl₄) 2965, 2947, 2924, 2916, 2853, 1727, 438, 1382, 1236, 1196, 1162 cm$^{-1}$.

¹H-NMR (CDCl3, 270 MHz) δ 5.02 (m, 4H), 4.86 (dd, 1H, J=8.8 Hz), 3.59 (s, 3H), 1.8–2.1 (m, 15H), 1.63 (d, 3H, J=1.18 Hz), 1.60 (s, 6H), 1.52 (s, 12H), 1.36 (d, 1H, J=5.3 Hz), 1.30 (t, 2H, J=8.2 Hz), 1.18 (s, 3H) ppm.

Mass Spec (CI—NH3,+ions) m/e 472 (M+NH4), 455 (M+H), 423 (M+H—CH3OH), 395, 385, 317, 177.

Anal. Calc'd for $C_{31}H_{50}O_2$: C, 81.88; H, 11.08 Found: C, 81.85; H, 11.06.

Data for 2A

IR (CCl4) 2966, 2950, 2926, 2916, 2855, 1731, 438, 1383, 1192, 1174, 1152, cm⁻¹. ¹H-NMR (CDCl, 270 MHz) 6 5.44 (dd, 1H, J=8.80, 1.17 Hz), 5.04 (m, 4H), 3.54 (s, 3H), 1.8–2.1 (m, 15H), 1.80 (t, 1H, J=8.80 Hz), 1.61 (s, 3H), 1.60 (s, 6H), 1.52 (s, 12H), 1.11 (s, 3H) ppm.

Mass Spec (CI—NH3,+ions) m/e 472 (M+NH4), 455 (M+H), 428 (M+H−CH3OH).

Anal. Calc'd for $C_{31}H_{50}O_2$: C, 81.88; H, 11.08 Found: C, 82.26; H, 11.43.

EXAMPLE 3

[1',2β(E),3β(E,E)]-2-(4,8-Dimethyl-3,7-nonadienyl)-2-methyl-3-(2,6,10-trimethyl-1,5,9-undecatrienyl)-cyclopropanemethanol A solution of 2.353 g (5.2 mmol) of Example 2D ester in 25 mL of diethyl ether at 0° C. under argon was treated with 263 mg (6.8 mmol, 1.3 mol-equiv) of lithium aluminum hydride and the resulting suspension was stirred at room temperature for three hours. Excess reagent was quenched with 265 μL H2O, 265 μL 15% NaOH and 800 μL H2O, then stirred for 15 minutes at 0° C. and 0.5 hours at room temperature. A portion of Na was added, the mixture was stirred for one hour, then filtered through a pad of Celite, washing with copious quantities of diethyl ether, then with CH2Cl2. Evaporation yielded 2.641 g of crude title product as a colorless oil. Purification by flash chromatography on 200 g of Merck 9385 silica, eluted with 5:95 ethyl acetate:hexane provided 2.059 g (93%) of title presqualene alcohol as a clear, colorless oil.

TLC Silica gel (1:9 ethyl acetate:hexane) $R_f$=0.20

IR (CCl4) 3627, 2969, 2925, 2917, 2855, 1450, 1382, 1109, 1015, 984, 957 cm⁻¹.

¹H-NMR (CDCl3, 270 MHz) 6 5.10 (m, 4H), 4.93 (d, 1H, J=8 Hz), 3.79 (dd, 1H, J=11.7, 5.8 Hz), 3.54 (dd, 1H, J=11.7, 8.8 Hz), 1.9–2.2 (m, 15H), 1.68 (s, 9H), 1.60 (s, 12H), 1.2–1.5 (m, 3H), 1.14 (s, 3H), 0.88 (dt, 1H, Jd=8.8, Jt=5.8 Hz), ppm.

Mass Spec (CI—NH3+ions) m/e 444 (M+NH4), 409 (M+H—H2O), 177, 151, 121, 109, 81, 69.

Anal. Calc'd for $C_{30}H_{50}O$: C, 84.44; H, 11.81 Found: C, 84.70; H, 12.15.

EXAMPLE 4

(E,E)-2,2-Dimethyl-3-(2,6,10-trimethyl-1,5,9-undecatrienyl)-1,1-cyclopropanedicarboxylic acid, dimethyl ester A solution of 600 mg (1.77 mmol) of Example 1, Part C farnesyl triflone and 615 μL (3.54 mmol, 2 equiv.) of hexamethylphosphoramide (distilled) in 8 mL of tetrahydrofuran was treated over four minutes with a solution of 1.25 mL (1.95 mmol, 1.1 equiv.) of 1.6 M n-butyllithium in hexanes, to provide a pale yellow solution. After 0.5 hours, a solution of 337 mg (1.95 mmol, 1.1 equiv.) of (1-methylethylidene)propanedioic acid, dimethyl ester in 2 mL of tetrahydrofuran was added dropwise. The reaction mixture was stirred for one hour at −78° C. and three hours at 0° C., then quenched with saturated NH4Cl and diluted with 80 mL of diethyl ether. The organic phase was washed with five 20 mL portions of H2O and 20 mL of brine, dried over MgSO4, and evaporated to yield 727 mg of crude title product. Purification by flash chromatography on 70 g of silica gel, eluted with 2:98 ethyl acetate/hexanes provided 522 mg (81%) of the title cyclopropane as a clear, colorless oil.

TLC Silica gel (5:95 ethyl acetate/hexanes) $R_f$=0.37.

IR (CCl4) 2950, 2926, 2855, 1731, 1459, 1445, 1434, 1379, 1306, 1289, 1242, 1196, 1117, 1101, 1073 cm⁻¹.

¹H-NMR (CDCl3, 270 MHz) 6 5.10 (m, 2H), 5.01 (d, 1H, J=8.20 Hz), 3.73 (s, 3H), 3.69 (s, 3H), 2.45 (d, 1H, J=8.20 Hz), 1.9–1.2 (m, 8H), 1.73 (s, 3H), 1.68 (s, 3H), 1.60, (s, 6H), 1.27 (s, 3H), 1.24 (s, 3H) ppm.

Mass spec. (CI—CH4/N2,+ions) m/e 417 (M+C3H5), 405 (M+C2H5), 377 (M+H), 345, 313.

Anal. Calc'd for $C_{23}H_{36}O_4$: C, 73.37; H, 9.64 Found: C, 73.47; H, 9.63.

The compounds prepared in accordance with the methods of the invention may be used to prepare squalene synthetase inhibitors, using techniques as disclosed in Capson et al, supra, which are useful in inhibiting cholesterol biosynthesis, and may be used to prepare insecticides in accordance with Arlt et al, supra.

What is claimed is;

1. A method for preparing an isoprenoid cyclopropane 1-mono-carboxylate of the structure

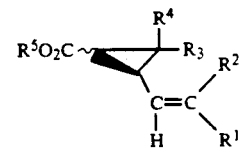

wherein $R^1$, $R^2$, $R^3$ and $R^4$ are the same or different and are independently selected from CH3 or

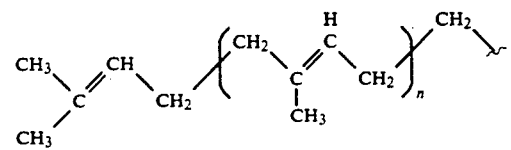

wherein n is 0 to 3 and $R^5$ is lower alkyl, which comprises treating an isoprenoid cyclopropane 1,1-dicarboxylate of the structure

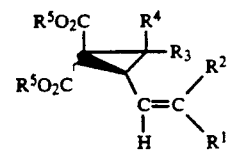

wherein $R^1$, $R^2$, $R^3$, $R^4$ and $R^5$ are as defined above, with a tetraalkylammonium acetate in the presence of an inert organic solvent under an inert atmosphere to form the monocarboxylate.

2. The method as defined in claim 1 wherein the isoprenoid cyclopropane 1,1-dicarboxylate is prepared by treating an allylic fluorinated sulfone of the structure

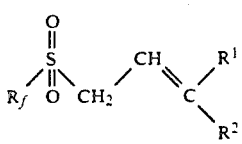

wherein $R_f$ is $CF_3(CF_2)_m$, where m is 0 to 5, and $R^1$ and $R^2$ are as defined above, with an alkene 1,1-dicarboxylate of the structure

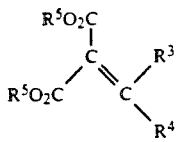

wherein $R^3$, $R^4$ and $R^5$ are as defined in claim 1, in the presence of base, at a reduced temperature of from about $-80°$ to about $25°$ C., to form the isoprenoid cyclopropane 1,1-dicarboxylate.

3. A method for preparing an isoprenoid cyclopropane, 1,1-dicarboxylate having the structure

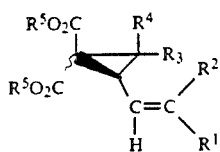

wherein $R^1$, $R^2$, $R^3$ and $R^4$ are the same or different and are independently selected from $CH_3$ or

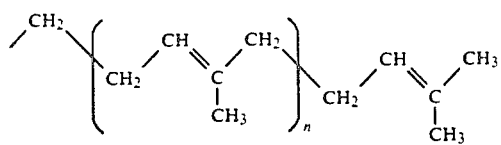

wherein n is 0 or 3, and $R^5$ is lower alkyl, which comprises treating a compound of the structure

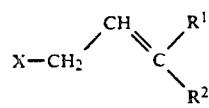

which X is Br, Cl or I, with a triflinate of the structure

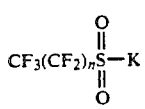

in the presence of 18-crown-6 in the presence of an inert organic solvent to form a compound of the structure

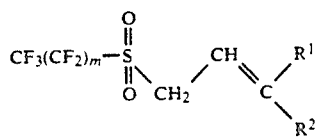

treating the so-formed allylic fluorinated sulfone with an alkene 1,1-dicarboxylate of the structure

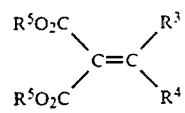

in the presence of base at a reduced temperature of within the range of from about $-80°$ to about $25°$ C. to form the isoprenoid cyclopropane 1,1-dicarboxylate.

4. A method for preparing an allylic fluorinated sulfone having the structure

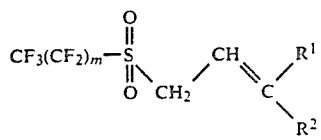

wherein $R^1$ and $R^2$ are the same or different and are $CH_3$ or

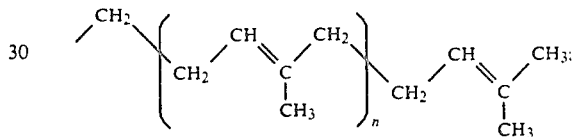

m is 0 to 5 and n is 0 to 3, which comprises treating a compound of the structure

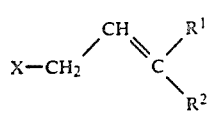

wherein X is Br, Cl, I, with a triflinate of the structure

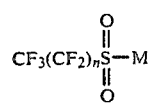

wherein M is an alkali metal in the presence of 18-crown-6 and an inert organic solvent.

5. A method for preparing an isoprenoid cyclopropane carboxylic acid of the structure

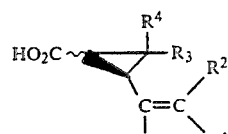

wherein $R^1$, $R^2$, $R^3$ and $R^4$ are the same or different and are independently selected from $CH_3$ or

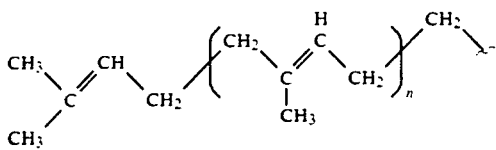

wherein n is 0 to 3, which comprises treating an isoprenoid cyclopropane 1,1-dicarboxylate of the structure

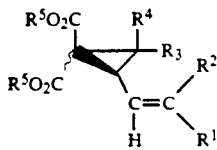

wherein $R^5$ is lower alkyl and $R^1$, $R^2$, and $R^3$, and $R^4$ are as defined above, with a tetraalkylammonium acetate in the presence of an inert organic solvent under an inert atmosphere to form the monocarboxylate, and then hydrolyzing the monocarboxylate to form the corresponding acid.

6. A method for preparing an isoprenoid cyclopropane hydroxymethyl compound of the structure

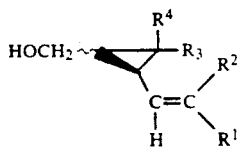

wherein $R^1$, $R^2$, $R^3$ and $R^4$ are the same of different and are independently selected from $CH_3$ or

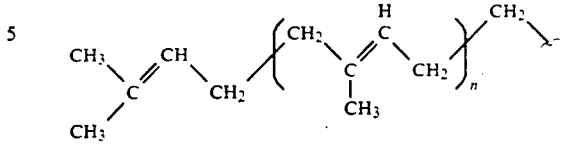

wherein n is 0 to 3, which comprises treating an isoprenoid cyclopropane, 1,1-dicarboxylate of the structure

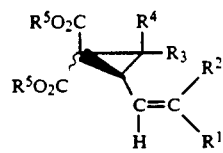

wherein $R^5$ is lower alkyl and $R^1$, $R^2$, $R^3$, and $R^4$ are as defined above, with a tetraalkylammonium acetate in the presence of an inert organic solvent under an inert atmosphere to form the monocarboxylate, then hydrolyzing the monocarboxylate to form the corresponding acid of the structure

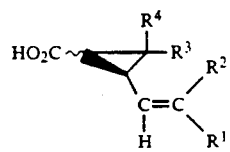

and treating the acid with a reducing agent to form the corresponding alcohol.

* * * * *